United States Patent [19]
Bindra et al.

[11] Patent Number: 6,126,950
[45] Date of Patent: Oct. 3, 2000

[54] COMPOSITION USEFUL FOR HEALING AND PROTECTING SKIN

[75] Inventors: Rattan Lal Bindra; Rashmi Gupta; Yogendra Nath Shukla; Samresh Dwivedi; Sushil Kumar, all of Lucknow, India

[73] Assignee: Council of Scientific and Industrial Research, New Delhi, India

[21] Appl. No.: 09/058,217

[22] Filed: Apr. 10, 1998

[30]   Foreign Application Priority Data

Jun. 24, 1997  [IN]  India ............................... 1715/DEL/97

[51] Int. Cl.⁷ ............................... A61K 7/00; A61K 6/00; A61K 7/021
[52] U.S. Cl. ..................... 424/401; 424/70.1; 424/70.11; 424/195.1; 514/844; 514/847; 514/887
[58] Field of Search ................................. 424/401, 70.1, 424/70.11, 195.1; 514/887, 844

[56]   References Cited

U.S. PATENT DOCUMENTS

| | | | |
|---|---|---|---|
| 4,534,981 | 8/1985 | Zabotto et al. | 514/783 |
| 4,569,839 | 2/1986 | Grollier | 424/74 |
| 5,370,873 | 12/1994 | Udeinya | 424/195.1 |
| 5,693,327 | 12/1997 | Shah | 424/195.1 |

FOREIGN PATENT DOCUMENTS

| | | | |
|---|---|---|---|
| 55627 | 6/1991 | Hungary | . |
| 6513789 | 1/1968 | Netherlands | . |
| 157294 | 5/1992 | Poland | . |

OTHER PUBLICATIONS

Wells, *Cosmetics and the Skin*, p. 301, New York, NY 1967.
Wells, *Cosmetics and the Skin*, 266–267, New York, NY 1967.

American Chemical Society, *Chemical Abstracts*, p. 1959, Columbus, OH 1959.

The Merck Index, Windholz, Ed. 10$^{th}$ edition (1983) (Merck: Rawhay NJ) p. 9834.

Segawa et al. "Effects of lactic esters and mentha oil on percutaneous absorption of flubiprofen cataplasms," Yakuzaigaku (1992) 52(1); 45–50 (abstract only).

Lawless The Illustrated Encyclopedia of Essential Oils: The Complete Guide to the Use of Oils in Aromatherpathy and Herbalism:, (1995) Barnes & Noble Books: London), p. 209, 185 and 209).

Swinyard et al. In "Remington's Pharmaceutical Sciences", (1980) (Mack Publishing: Easton PA), p. 773, 1243, 1248–1250.

*Primary Examiner*—John Kight
*Assistant Examiner*—D. Faulkner
*Attorney, Agent, or Firm*—Dickinson Wright PLLC

[57]   ABSTRACT

The present invention relates to a formulation of herbal cream for cracked heels and palms. Since the components in the formulation are from herbal sources it is very safe and eco-friendly and does not produce any harmful effects on the skin. It is comprised of a natural wax as an emulsifier, extract of curcuma and the gum of Acacia or Colophonium or Shorea. The gum gives a synergistic effect in binding and healing the skin with natural wound healing herbal extract selected from the aqueous extracts of curcuma, neem and allantonin. This is combined with a wound healing fragrant oil. The natural wound healing herbal extract acts as a humectant and the gum gives an synergistic effect in binding the skin thereby reducing water loss from the skin. The cream spreads evenly and smoothly when applied on the affected parts, and quickens healing, restores natural suppleness and softness and also serves as an antiseptic.

13 Claims, No Drawings

COMPOSITION USEFUL FOR HEALING AND PROTECTING SKIN

BACKGROUND OF INVENTION

This invention relates to a formulation useful as a Herbal Cream for Cracked Heels and PALMS.

The herbal cream formulation of the present invention consists of a natural herbal extract of curcuma and plant gum. The healing property of curcuma is well established and gums of Acacia or Colophonium or Shorea have been used. The synergistic action of curcuma extract with one of the gums quickens the healing, binds the skin and makes it soft and supple. A natural fragrant oil has been added which enhances the healing property. The formulation is a synergistic mixture with enhanced healing properties for cracked heels and hands.

Human skin consists of two major layers, a relatively thicker layer called dermis and a superficial layer called epidermis. The skin serves both to keep out noxious material, disease producing organisms and to keep in valuable commodities such as water. Skin may be hairy or glabrous i.e. devoid of hair such as feet and palms.

Under normal conditions of average humidity, water is lost continuously from the surface of the skin. At a very high humidity, the skin is almost water-logged, but at a very low relative humidity, the rate of loss from the skin will exceed the rate of passage from body tissue. Water content in the horny layer of the skin falls below the level required to maintain its palacity and its flexibility becomes less than that of normal skin. Changes of this nature occur at low humidity resulting in cracks of heels and sometimes in hands. Cracks in heels may be superficial, deep and very deep. The other cause of cracks in heels can be due to unknown pathological reasons and frequent exposure to detergents and dust. The cracks are abnormalities in the skin resulting in pain, bleeding, sensitivity to cold and warmth. The cracks are socially unattractive and reduce the efficiency in the man.

The healing, protection and prevention of cracks in heels and hands is generally done by emollient creams/lotions.

In the present invention, the extract of natural botanicals/herbs are formulated in a natural fatty base. When applied, it reduces the rate of water loss from the surface of the cracked heels and hands to the extent that water is conserved and the horny layer hydrates. The fatty film occludes the water coming from the skin tissue and at the same time natural herbal extracts heal the wound and prevent it from fungal infection making the skin soft and supple.

The following foot cream formulation has been cited in literature (Winer, A. L. and Cooparwills, E. S. Lancet 2, 663, 1956). Referred in Cosmetic and Skin F. V. Wells and Irwini I. Lobowe. (Reinhold Publishing Corporation, London 1967).

| | |
|---|---|
| Phenol | 1.0 parts by wt. |
| Camphor | 6.0 parts by wt. |
| Peru of Balsam | 2.0 parts by wt. |
| Petrolatum | 25.0 parts by wt. |
| Praffin Wax | 7.5 parts by wt. |
| Anhydrous Lanolin | 58.5 parts by wt. |

The above described formulation suffers from a number of disadvantages
1. Phenol, a chemical in the formulation, will not allow the cracks and wounds to heal quickly.
2. The presence of a long range of emulsifiers i.e. petrolatum, paraffin wax, anhydrous lanolin, is not required as it will make the formulation expensive.
3. Anhydrous lanolin will not allow adhering of the cream to the applied parts.
4. The formulation will not be agreeable the to consumer as it does not contain any fragrance.

Another formulation is a water barrier cream used for cracked feet referred in the above mentioned book (German patent 12,752. Rohn, Schwartezkopf and Krohn, 1957) corresponding British patent 780,918. 1957) described as:

| | | |
|---|---|---|
| Butadiene polymer (m.v. 32000) | 14.0 | parts by wt. |
| Petroleuin jelly, white | 11.5 | parts by wt. |
| Paraffin wax (m.p. 50–52×C) | 7.5 | parts by wt. |
| Emulsifying wax (Cetyl and stearyl alcohol with sodium alkyl sulphate) | 5.0 | parts by wt. |
| Talc | 3.5 | parts by wt. |
| p-Chlorometa creosol, Na salt | 0.1 | parts by wt. |
| Lactic acid, 90 per cent | 0.15 | parts by wt. |
| Water | 58.25 | parts by wt. |

This formulation contains a rubbery material butadiene polymer of high molecular weight which can hardly be emulsified hence a long range of emulsifiers like paraffin wax, emulsifying wax have been added which is not desirable. Moreover, the initial tackiness after application will disappear and the cream will dry forming a hard layer which will be difficult to remove.

At present, following creams available in the market do not restore the natural smoothness and suppleness due to their non occlusive nature.

| 1) KRACK | | |
|---|---|---|
| Daruaridf and Shkjaras (Berberis sp and Cederus oil) | AB | 35.4% |
| Dodioshak and sarjaras (Laptadenia sp and pine gum) | AB | 3.5% |
| Raktapurakf (garcinia indica.) | AB | 3.6% |
| Balance (natural wax) | AB | 57.5% |
| | | 100% |
| Manufactured by Pakas Pharmaceuticals Ltd. (India) | | |
| 2) LICHENSA | | |
| Monochloravacrol | 0.1% | w/w |
| Menthol I.P. | 0.80% | w/w |
| Ichthammol(I.P.'66) | 1.50 | w/w |
| Zinc oxide | 7.5% | w/w |
| Lanolin Base | 7.5% | w/w |
| Balance | 81.6% | w/w |
| Manufactured by Dollar Company (Pvt.) Ltd. (India) | | |

In the above formulation (1) no doubt a wound healer has been added but a desired emollient is not present hence a consistency and ease of application is lacking. Due to the addition of Raktapurakf (oil) the formulation does not have a reasonably persistent adherence to the skin. Similarly formulation No. (2) described above suffers from a number of disadvantages. Monochloravacrol, a bactericide, is and irritant to mucous membrane. Ichthammol in combination with lanolin does not form a proper emulsion and a water protective layer can not be formed in this combination. Hence it will take a long time for healing. Moreover a proper healing agent has not been added.

SUMMARY OF THE INVENTION

The present invention relates to a formulation of herbal cream for cracked heels and palms. Since the components in the formulation are from herbal sources it is very safe and ecofriendly and does not produce any adverse effect on the skin. It comprises of a natural wax as an emulsifier, extracts of wound healing herbal extract, acacia gum or colophonium or shorea, and a wound healer fragrant oil. The wound healing herbal extract acts as a humectant, prevents infection and heals the cracks quickly and effectively. The cream spreads evenly and smoothly when applied on the affected parts. The gum and wax occludes and prevents water loss from effected parts, which quickens healing and restores the natural softness and suppleness and also serves as an antiseptic. The acacia gum or colophonium or shorea gives synergistic effect in combination with curcuma extract thereby quickening healing.

Accordingly, the present invention provides a formulation useful as a herbal cream for cracked heels and palms which comprises:

| | |
|---|---|
| Wound healing herbal extract | 2 to 10 parts by wt. |
| Acacia gum or Colophonium or Shorea | 2 to 20 parts by wt. |
| Natural wound healing fragrant oil | 0.5 to 2 parts by wt. |
| Natural wax | 50 to 70 parts by wt. |
| Petroleum jelly | 10 to 20 parts by wt. |
| Preservative | 0.5 to 20 parts by wt. |

The natural wound healing extract used is such as aqueous curcuma extract, or Allantonin extract or Neem extract. The natural wound healing fragrant oil used is such as chamomile oil, basil oil or mentha oil.

The natural wax used is such as purified bees wax, or spermaceti or Lanolin.

The petroleum jelly used is of commercial grade.

The preservative used is such as nipagin-m, tocopherol or rosemary oil.

The process for preparation of the cream involves purification of Bees wax and melting it over a steam bath at 64° C., adding wound healing herbal extract with a low water content and subsequently adding gum. It has been found that addition of white petroleum jelly emulsifies bees wax and gives a better texture and consistency.

DETAILED DESCRIPTION OF THE INVENTION

The following examples are given by way of illustration of the present invention and should not be construed to limit the and scope of the present invention.

EXAMPLE 1

Spermaceti was melted and while the spermaceti melting over a water bath, petroleum jelly was added and stirred at a slow speed with a mechanical stirrer until the two components became homogenous. Colophonium was added and stirring was carried out vigrously. Allantonin, a natural wound healer, was added and stirred slowly. Wound healing fragrant oil was added after the formulation was cooled to 35° C. followed by the addition of preservative and emollient oil.

| | |
|---|---|
| Spermaceti | 65 parts by wt. |
| Petroleum jelly | 15 parts by wt. |
| Natural wound healer (Allantonin) | 2 parts by wt. |
| Colophonium | 15 parts by wt. |
| Natural wound healing fragrent oil (chamomile oil) | 2 parts by wt. |
| Preservative (tocopherol) and emollient | 1 part by wt. |

EXAMPLE 2

Commercial lanolin was purified and melted, while melting, petroleum jelly was added and stirred until the two components became homogenous. Gum acacia was melted seperately and slowly added to it while stirring it vigrously. A natural wound healer aqueous extract of leaf and bark of neem having a moisture content of 15% was added and stirred slowly. After the composition was cooled to ambient temperature fragrent wound healifg mentha oil was added, followed by the addition of a preservative and emollient oil.

| | |
|---|---|
| Lanolin | 60 parts by wt. |
| Petroleum jelly | 10 parts by wt. |
| A natural wound healinq aqueous extract of bark and leaf of neem | 10 parts by wt. |
| Gum Acacia | 16 parts by wt. |
| Natural wound healinq fragrant oil (Mentha oil) | 2 parts by wt. |
| Preservative (Rosemery oil) and emollient | 2 parts by wt. |

EXAMPLE 3

Commercial grade bees wax was purified and melted at 64° C. While melting over a water bath, petroleum jelly was added and stirred until the two components became homogenous. Powdered and sieved to 100 mesh, shorea resin was added and stirred thoroughly by a mechanical stirrer. Aqueous extract of curcuma having water content of 15–18% was added to it and stirred vigrously until the mixing was complete and uniform. This was cooled down to 35° C. and wound healing fragrant oil was added followed by the addition of preservative and emollient oil and the whole formulation was mixed completely by a mechanical stirrer.

| | |
|---|---|
| Bees wax | 65 parts by wt. |
| Petroieum jelly | 17 parts by wt. |
| Natural wound healing aqueous curcuma extract | 10 parts by wt. |
| Shorea gum | 4 parts by wt. |
| Natural wound healing fragrant oil (basil oil) | 2 parts by wt. |
| Preservative nepagin-m and emollient oil | 2 parts by wt. |

In these formulations, a natural wound healing extract when combined with the natural gum gives synergistic effect and thus enhances the wound healing activity.

The above formulations were tested for healing of cracks in heels and hands on human subjects of both sexes of different age groups.

Formulation No 1 gave desired results but was expensive as the ingredients used are comparatively costlier.

Formulation No. 2 gave the desired results but the healing took a long time when compared with formulation No. 1 and 3.

Formulation No. 3 gave the best desired results and is cost effective. Field trials of this formulation was conducted on more than 100 human subjects at Lucknow between the age group of 22 years and 65 years of both sexes.

Mild cracks were healed within 3 days when applied twice daily. Moderate cracks were healed within 7 days and severe cracks were healed within 10 days. The natural suppleness was restored in all the cases after healing. One subject reported healing of psorosis on elbows and ankle joints and another subject with severe bleeding in craks reported total healing within 8 days. In all the subjects, soothing effect was observed after one or two applications.

The above observations ascertain that formulation No. 3 is best for cracked heels and palms in all cases.

The main advantages of the present invention are:

1) It spreads evenly on the applied parts.
2) It heals the cracks rapidly and makes the skin soft and supple.
3) The formulation acts as an antiseptic.
4) The formulation is an emollient cream which prevents water loss from the cracks and promotes healing.

We claim:

1. A composition for use on cracked heels, palms and the like, comprising:

natural extract of curcuma;

natural gum selected from acacia, shorea or colophonium;

natural fragrant oil selected from basil, chamomile oil or mentha oil;

natural bees wax for use as an emulsifier; and petroleum jelly, wherein 2 to 10 parts by weight of said extract of curcuma is provided, and 2 to 20 parts by weight of said natural gum is provided, wherein the combination provides a synergistic effect which enables said composition to quicken healing when applied to cracked skin.

2. The composition of claim 1, wherein a preservative is added which is selected from the group consisting of rosemary oil, tocopherol and nipagin-m, and which comprises 0.5 to 20 parts by weight of said composition.

3. The composition of claim 1, wherein said composition comprises 0.5 to 2 parts by weight of said natural fragrant oil, 50 to 70 parts by weight of said natural bees wax, and 10 to 20 parts by weight of said petroleum jelly.

4. A composition for use on cracked heels, palms and the like, comprising:

natural extract of curcuma;

natural gum selected from acacia, shorea or colophonium;

natural fragrant oil;

a natural wax for use as an emulsifier; and petroleum jelly, wherein 2 to 10 parts by weight of said extract of curcuma is provided, and 2 to 20 parts by weight of said natural gum is provided, wherein the combination provides a synergistic effect which enables said composition to quicken healing when applied to cracked skin.

5. The composition of claim 4, wherein said natural fragrant oil is selected from the group consisting of basil, chamomile oil and mentha oil.

6. The composition of claim 4, wherein said natural wax is selected from the group consisting of bees wax, spermaceti and lanolin.

7. The composition of claim 4, wherein a preservative is added which is selected from the group consisting of rosemary oil, tocopherol and nipagin-m, and which comprises 0.5 to 20 parts by weight of said composition.

8. The composition of claim 4, wherein said composition comprises 0.5 to 2 parts by weight of said natural fragrant oil, 50 to 70 parts by weight of said natural wax, and 10 to 20 parts by weight of said petroleum jelly.

9. A composition for use on cracked heels, palms and the like, comprising:

a wound healing herbal extract selected from curcuma, allantonin or neem;

natural gum selected from acacia, shorea or colophonium;

natural fragrant oil selected from basil, chamomile oil and mentha oil;

a natural wax for use as an emulsifier; and petroleum jelly, wherein 2 to 10 parts by weight of said herbal extract is provided, 2 to 20 parts by weight of said natural gum is provided, 0.5 to 2 parts by weight of said natural fragrant oil is provided, and 50 to 70 parts by weight of said natural wax is provided, wherein said combination quickens healing when applied to cracked skin.

10. The composition of claim 9, wherein said natural wax is selected from the group consisting of bees wax, spermaceti and lanolin.

11. The composition of claim 9, wherein said composition comprises 10 to 20 parts by weight of said petroleum jelly.

12. The composition of claim 9, wherein said composition also comprises 0.5 to 20 parts by weight of a preservative, wherein said preservative is selected from the group consisting of rosemary oil, tocopherol and nipagin-m.

13. The composition of claim 9, wherein said wound healing herbal extract is curcuma, and the combination of said curcuma and said natural gum provides a synergistic effect which enables said composition to quicken healing when applied to cracked skin.

* * * * *